(12) United States Patent
Schreiner et al.

(10) Patent No.: US 11,457,323 B2
(45) Date of Patent: Sep. 27, 2022

(54) CUSTOM ELASTOMERIC EARMOLD WITH SECONDARY MATERIAL INFUSION

(71) Applicant: GN HEARING A/S, Ballerup (DK)

(72) Inventors: Russell L. Schreiner, Evanston, IL (US); Gustavo A. Morales, Roselle, IL (US)

(73) Assignee: GN HEARING A/S, Ballerup (DK)

( * ) Notice: Subject to any disclaimer, the term of this patent is extended or adjusted under 35 U.S.C. 154(b) by 249 days.

(21) Appl. No.: 15/496,773

(22) Filed: Apr. 25, 2017

(65) Prior Publication Data

US 2017/0305040 A1 Oct. 26, 2017

Related U.S. Application Data

(60) Provisional application No. 62/327,723, filed on Apr. 26, 2016.

(51) Int. Cl.
*H04R 25/00* (2006.01)
*B29C 44/18* (2006.01)
(Continued)

(52) U.S. Cl.
CPC ............ *H04R 25/652* (2013.01); *A61F 11/08* (2013.01); *B29C 33/3842* (2013.01);
(Continued)

(58) Field of Classification Search
CPC ............ B29C 33/3857; B29C 33/3835; B29C 33/3842; B29C 44/186; B29C 45/0055;
(Continued)

(56) References Cited

U.S. PATENT DOCUMENTS 4,774,938 A 10/1988 Leight
5,487,012 A 1/1996 Topholm et al.
(Continued)

FOREIGN PATENT DOCUMENTS

DE 10248755 5/2004
JP 1993-220777 8/1993
(Continued)

OTHER PUBLICATIONS

International Search Report and Written Opinion dated Jul. 14, 2017 for Corresponding European Patent Application No. PCT/EP2017/059891.

(Continued)

*Primary Examiner* — Jacob T Minskey
*Assistant Examiner* — S. Behrooz Ghorishi
(74) *Attorney, Agent, or Firm* — Vista IP Law Group, LLP

(57) ABSTRACT

A method of making a mold, the mold having an interior cavity for containing a first material and a second material, wherein the mold comprises a first port configured to receive the first material, a second port configured to receive the second material, and a first channel for directing the second material to within the first material, the method includes: determining an electronic file having data representing a shape of an ear; processing the electronic file to create an electronic model of the mold, the electronic model of the mold having sprue features; and creating the mold based on the electronic model of the mold.

34 Claims, 11 Drawing Sheets

(51) Int. Cl.
  *B33Y 80/00* (2015.01)
  *B29C 33/38* (2006.01)
  *G06T 17/00* (2006.01)
  *A61F 11/08* (2006.01)
  *B29C 45/00* (2006.01)
  *H04R 1/10* (2006.01)
  *G06F 30/00* (2020.01)
  *B29K 75/00* (2006.01)
  *B29K 83/00* (2006.01)

(52) U.S. Cl.
  CPC ........ *B29C 33/3857* (2013.01); *B29C 44/181* (2013.01); *B29C 44/186* (2013.01); *B29C 45/0055* (2013.01); *B33Y 80/00* (2014.12); *G06T 17/00* (2013.01); *H04R 1/1058* (2013.01); *H04R 25/658* (2013.01); *B29C 33/3835* (2013.01); *B29C 2033/3871* (2013.01); *B29K 2075/00* (2013.01); *B29K 2083/00* (2013.01); *G06F 30/00* (2020.01); *H04R 2225/77* (2013.01)

(58) Field of Classification Search
  CPC ............. B29C 45/13; B29C 2045/135; B29C 2045/161; B29C 2045/167; B29C 45/1642; B29C 2045/1653; B29C 2045/1654; B29C 45/1703; A61F 11/08; H04R 1/1058; H04R 25/652; H04R 25/658
  See application file for complete search history.

(56) References Cited

U.S. PATENT DOCUMENTS

| | | | |
|---|---|---|---|
| 7,984,716 | B2 | 7/2011 | Purcell et al. |
| 8,032,337 | B2 | 10/2011 | Deichmann et al. |
| 2001/0008560 | A1 | 7/2001 | Stonikas et al. |
| 2002/0025055 | A1 | 2/2002 | Stonikas |
| 2003/0133583 | A1 | 7/2003 | Widmer et al. |
| 2006/0239481 | A1 | 10/2006 | Martin |
| 2008/0113061 | A1* | 5/2008 | Stoiber .................. B29C 49/36 |
| | | | 425/522 |
| 2011/0271965 | A1 | 11/2011 | Parkins et al. |
| 2012/0243701 | A1 | 9/2012 | Parkins et al. |
| 2015/0030196 | A1* | 1/2015 | Basseas ............... H04R 1/1016 |
| | | | 381/380 |
| 2016/0221234 | A1* | 8/2016 | Sorrentino .......... B29C 45/1642 |

FOREIGN PATENT DOCUMENTS

| | | |
|---|---|---|
| WO | WO 0070911 | 11/2000 |
| WO | WO-0070911 A1 * | 11/2000 .......... H04R 25/456 |
| WO | WO 2008/157557 | 12/2008 |
| WO | WO 2010/094034 | 8/2010 |
| WO | WO 2011/044903 | 4/2011 |
| WO | WO 2011/163565 | 12/2011 |
| WO | WO 2012/007193 | 1/2012 |

OTHER PUBLICATIONS

First Office Action dated Jun. 1, 2020 for related Chinese Patent Application No. 201780032553.7.
Foreign OA for JP Patent Appln. No. 2018-555890 dated Nov. 30, 2021, with English translation.

* cited by examiner

CUSTOM ELASTOMERIC EARMOLD WITH SECONDARY MATERIAL INFUSION

RELATED APPLICATION DATA

This application claims priority to and the benefit of U.S. Provisional Patent Application No. 62/327,723, filed on Apr. 26, 2016, the entire disclosure of which is expressly incorporated by reference herein.

FIELD

This disclosure relates to systems and methods for making a hearing device components, and more specifically, to systems and methods for making earmolds.

BACKGROUND

Various techniques may be employed to design and fabricate custom earmold and hearing aid shell. For examples, digital data processing and 3D Printing (rapid prototyping) have been utilized to make custom earmolds. These techniques provide the ability to add sophisticated features to a custom product while maintaining a reasonable, machine based fabrication.

Many sound producing (hearing aids and earphones) and hearing protective (earplugs and musician plugs) devices require that 1) that the device provides a good acoustic seal which is important for device performance and sound quality, and 2) that the device fits comfortably in the ear. There are many concepts for achieving this through the use of a variety of materials including elastomers and foams in a variety of shapes, sizes and processes.

However, in all examples of composite devices the elastomeric part and the foam part are added as separate items with the foam piece added to the elastomer in a secondary operation, or are pumped into an inflatable container.

SUMMARY

A new process for making custom elastomeric earmoulds used in both active sound processing units (hearing aids, earphones) and passive devices (earplugs, swim plugs) is described herein. The process creates a product that is made from soft, biocompatible material such as silicone or urethane that is infused with compatible, compressible foam, or other soft materials, in order to achieve softness and compliance in specific areas on the earmold. The result is an earmold with localized softness and compliancy that surpasses previous art by achieving higher degrees of comfort, improved acoustic seal, and by allowing a deeper fit in the ear canal can prevent occlusion effects.

The combination of the material and the two design concepts accomplishes one of more of the followings: 1) It creates a product with excellent retention in the ear due to the outer ear customization; 2) It creates a product with improved compliance to move as the ear canal moves, improved comfort, increased flexibility, excellent acoustic seal and a deeper seal resulting in reduced occlusion in the ear canal. This improvement is the result of the foam infused areas that are softer, more compressible, but springier (e.g., more deformable, more elastic, etc.) than a solid elastomeric material and, therefore, becomes more accommodating to the dynamics of the canal when compared to full custom molds. The light spring force of the foam material provides an improved acoustic seal without discomfort; 3) It creates a comfortable product with improved and deeper acoustic seal over a full custom product as the silicone/silicone foam combination provides a compliant seal that does not break when the wearer moves his head or jaw.

In some embodiments, the product may be created using a digital processes common to the manufacture of hearing aid products. In this case, the process is used to make a one-time mold for casting silicone or urethane elastomers, but in addition to injecting the primary elastomer, an additional process step is performed to add a secondary interior material that is fully contained within the primary elastomer. The process takes advantage of the surface tension effect of the primary material to stay adhered to the interior surface of the exterior walls of the mold. This allows the secondary material to occupy the interior without displacing the base elastomer from the exterior.

Embodiments described herein will improve the performance of any in-ear product including, but not exclusive to: 1) hearing aids, 2) hearing protection, and 3) custom earphones.

Embodiments described herein involve use of a custom mold for the ear. In some embodiments, the custom mold has a custom portion confined to the outer ear and entry to the canal only. In other embodiments, the custom mold may have non-custom portion(s), and/or may not be confined to the outer ear and entry to the canal. For example, in other embodiments, the custom mold may extend to other parts of the user's ear, such as an outer part of the ear cannal and/or an inner part of the ear canal. The mold is made from injecting an elastomeric material into a one use injection made in a 3D printing process. Any portion of the mold can be enhanced through the infusion of a secondary material which displaces the original material from only the interior of the mold due to the surface tension characteristics of the primary elastomeric material which keep the primary material adhered to the injection mold surface.

Foam has an advantage over monolithic or solid materials in any application requiring compliance and comfort of an item in contact with a human. Foam is commonly used to enhance comfort in products ranging from furniture to shoes to helmets. Foam has also been used in earplugs for decades, but generally in pre-molded form. Foam has also been applied to earmolds to improve comfort and also to improve performance by providing a better acoustic seal.

However foam has some limitations in the custom earmold applications due to problems associated with production (short working times, limitation of material selection) and customer use associated with insertion (the foam is too flaccid to allow insertion), cleanliness (foams allow foreign material to become trapped in the foam cells) and strength (the tear strength of foam limits its ability to be removed from the ear if the mold fits too tight or is handled too roughly). Due to these limitations, most custom soft earmoulds are made from monolithic elastomers (silicone, PVC and urethane) rather than foam.

In some cases, one may attempt to provide a combination of silicone and foam or urethane and foam in order to take advantage of the beneficial properties of each. For example, the foam may be added as a separate piece of the mold using some assembly process. In non-custom ear tip applications, foam may be used by itself or combined with other pre-molded items to form a more complex device.

Embodiments described herein provide an improved method for combining foam and silicone in a custom application by using the casting techniques provided by 3D printing. A 3D mold can be used as a single use injection mold for a variety of material. At least one embodiment uses the basic concept of the one shot mold, but uses the concept of a secondary infusion of material to create a composite mold of both the primary material injected in the mold and the secondary material injected in the mold. The process also utilizes the chemical characteristic of surface tension to maintain the primary material as the "outer" skin or layer of the final device, while limiting the secondary material to the interior of the device. In this way the outer layer maintains the advantages of the primary material while the interior maintains the advantages of the secondary material.

The combination of materials is unlimited as long as they are chemically compatible and can be injected into a 3D printed mold. By means of non-limiting examples, some combinations are:

Primary material: silicone; Secondary material: silicone foam

Primary material: silicone of hardness A; Secondary material: silicone of a different hardness (e.g., lower hardness)

Primary material: silicone; Secondary material: silicone gel

Primary material: silicone; Secondary material: silicone of another color

Primary material: urethane; Secondary material: urethane foam

Primary material: urethane of hardness A; Secondary material: urethane of a different hardness (e.g., lower hardness)

Primary material: urethane; Secondary material: urethane gel

Primary material: urethane; Secondary material: urethane of another color

Primary material: urethane, or urethane and urethane foam.

Primary material: silicone; Secondary material: air

Primary material: silicone; Secondary material: a compatible liquid.

Primary material: silicone; Secondary material: urethane

A composite mold has the advantage of combining the desirable properties of both materials. For example, the silicone (primary) and silicone foam (secondary) composite has the advantage of the softness and compliance of the foam, but has the stiffness, strength and chemical stability of silicone. This results in an earmold of superior performance since it is very comfortable due to the foam, can go deep in the ear because of this comfort, will provide a better acoustic seal due to the compliance of the foam, but due to the stiffness of the silicone outer layer the earmold can be inserted easily, provides a biologically compatible surface, is easily cleaned and provides durable performance regarding tear strength and chemical resistance.

The composite earmold accomplishes one or more of the followings: 1) It achieves a better acoustic seal than a tight-fitting, full custom canal due to the improved compliance (softness) and shape changing abilities of foam; 2) It improves the comfort of the device for the same reasons of improved compliance and shape changing while forgiving incomplete ear impressions; 3) The composite mold can go deeper into the canal due to the improved softness and flexibility which has the advantages of reducing the occlusion effect; 4) It achieves lower noise levels associated with jaw movement and leaks associated with the continual loss and regain of an acoustic seal experienced using a tight fitting, monolithic material.

Another advantage of the molding process that entraps the secondary material on the interior of the mold is the allowance of liquids or gels as the secondary material. This allows the use of superior acoustic dampening caused by a variety of material choices.

The custom injection mold and casting may be used/performed in various processes, such as digital data processing, 3D Printing (rapid prototyping), etc.

In this case the shape of a person's ear is acquired through the injection of silicone into the ear and ear canal, or the outer ear and canal entry areas are scanned with a laser or white light scanner. The scanned image is used to fashion, or sculpt, the final shape of the product, and to add predesigned features to the mold that are merged into the digital image of the mold. A digital file of the final product design is then output to a 3D Rapid Prototyping/Manufacturing machine. In this process the object that is made on the 3D printer is an injection mold which is then filled with silicone (Martin). Once the silicone cures, the outer "shell" of the mold is cracked open and removed to reveal the silicone mold on the inside.

In some embodiments, the image of a person's ear may be captured, and a software may be provided to design the mold. In some embodiments, objects within the software may be used to add complexity to the injection mold and earmold design. The one unique object that is added to the earmold design is the injection mold sprue system: 1) a pre-designed shape which is chosen and located to optimize the amount and position of the secondary material, this is usually in the canal area but can also be in the outer ear area where the ear moves or is pressed upon when the wearer rests one side of the head against a surface.

Embodiments described herein involve a secondary casting operation which infuses a second material (e.g., foam) into the interior of the elastomeric casting. Accordingly, the elastomeric composite system and technique described herein are unique in that the delivery of the second material (e.g., foam) is an integral part of casting process.

In some cases, custom elastomeric molds may be casted using a single use 3D printed mold. Embodiments described herein utilize this process, but moves beyond that by not only creating a specialized exterior shape, but by also creating a specialized interior made from compatible foam.

In some embodiments, the process makes use of the surface tension involved in the elastomer casting process. When an elastomer is injected into a 3D printed one-shot injection mold, the surface tension of the original, or primary, material causes the elastomer to adhere to the surface of the mold. When any secondary material (such as another elastomer, air, water, other liquids, pastes or foam) possessing the characteristic of fluidity is injected into the mold, it cannot displace the original material from the interior surface of the mold. Rather, it can only displace the original primary material from the interior of the mold. This means that the original elastomer will remain along the interior surface of the mold and will form the outer "skin" or "layer" of the final device, while the secondary material will form the interior of the device.

There is a variety of process controls available that provide for control of both the location and amount of the residual primary material and the secondary infused material.

One process control is the timing of the primary material curing and the secondary material infusion. If the curing of the primary material is time dependent, then the thickness of the outer layer of the primary material may be controlled by time. This is because the curing of the primary material, if it is a two-part catalyst curing system, is a function of time.

The same would be accomplished by heat exposure with a heat dependent primary material.

Another process control is the use of specialized sprues and vents in the injection molding process. Placement and shape of sprues and vents controls the injection process and determines the location and volume of each material during injection.

In some embodiments, an interior portion of the primary material may be evacuated before the secondary material is placed inside the primary material. In such cases, another process control may be the evacuation of the primary material before the infusion of the secondary material. The primary material may be removed by using pressurized air or liquid, such as water, that acts as a temporary displacement of the primary material prior to the infusion of the secondary material into the interior cavity of the primary material.

An apparatus for forming a component for a hearing device, the component comprising an earpiece having a housing, the housing comprising a wall made from a first material, wherein the wall of the housing comprises a second material surrounded by the first material, the apparatus includes: a mold having an interior cavity for containing the first material and the second material; wherein the mold comprises a first port configured to receive the first material; wherein the mold comprises a second port configured to receive the second material, and a first channel for directing the second material to within the first material.

Optionally, the mold comprises a single-use mold.

Optionally, the apparatus further includes a first source of the first material.

Optionally, the first material comprises silicone or urethane.

Optionally, the apparatus further includes a second source of the second material.

Optionally, the mold also comprises a second channel for directing the second material to within the first material.

Optionally, the second material comprises silicone gel, silicone foam, urethane gel, or urethane foam.

Optionally, the apparatus further includes a source of liquid or air for displacing some of the first material after the first material is delivered inside the mold.

Optionally, the mold comprises a custom mold.

A component for a hearing device includes: an earpiece having a housing, wherein the housing comprises a wall made from a first material; wherein the wall of the housing comprises a second material surrounded by the first material.

Optionally, the housing comprises a channel, and wherein the wall surrounds the channel.

Optionally, the earpiece comprises a custom shell.

Optionally, the second material is configured to improve a bass effect associated with the hearing device.

Optionally, the second material is configured to provide an acoustic seal by attenuating external sounds.

Optionally, the second material is configured to reduce an occlusion effect associated with the hearing device.

Optionally, the first material comprises first silicone.

Optionally, the second material comprises second silicone different from the first silicone.

Optionally, the first silicone has a first hardness, and the second silicone has a second hardness different from the first hardness.

Optionally, the second silicone comprises silicone gel.

Optionally, the second silicone comprises silicone foam.

Optionally, the first material comprises first urethane.

Optionally, the second material comprises second urethane different from the first urethane.

Optionally, the first urethane has a first hardness, and the second urethane has a second hardness different from the first hardness.

Optionally, the second urethane comprises urethane gel.

Optionally, the second urethane comprises urethane foam.

Optionally, the second material comprises liquid.

Optionally, the second material comprises foam.

Optionally, the second material comprises air.

A method of making a mold, the mold having an interior cavity for containing a first material and a second material, wherein the mold comprises a first port configured to receive the first material, a second port configured to receive the second material, and a first channel for directing the second material to within the first material, the method includes: determining an electronic file having data representing a shape of an ear; processing the electronic file to create an electronic model of the mold, the electronic model of the mold having sprue features; and creating the mold based on the electronic model of the mold.

Optionally, the electronic model comprises a CAD model.

Optionally, the data represents a shape of a concha, an outer ear canal, and an inner ear canal.

Optionally, the mold is created using a 3D printer.

Optionally, the sprue features comprise a first sprue feature representing a first sprue for delivering the first material.

Optionally, the sprue features also comprise a second sprue feature representing a second sprue for delivering the second material.

A method of making a component of a hearing device using the mold, the method includes: injecting a first material into the mold; and injecting a second material into the mold so that the second material is surrounded by the first material; wherein the first material and the second material form parts of the component.

Optionally, the method further includes breaking the mold to remove the component.

Optionally, the method further includes removing an interior of the first material to create a cavity within the first material, wherein the second material is injected into the cavity within the first material.

Optionally, the act of removing comprises delivering liquid or air into the first material.

Optionally, the component comprises an earpiece.

An apparatus for forming a first component for a first hearing device, the first component comprising an earpiece having a housing, the housing comprising a wall made from a first material, wherein the wall of the housing comprises a second material surrounded by the first material, the apparatus includes: a mold having a first interior cavity for containing the first material and the second material, wherein the mold comprises a first port configured to receive the first material; and a first source of the second material for delivering the second material into the first interior cavity so that the second material is within the first material.

Optionally, the first source of the second material comprises a first syringe.

Optionally, the apparatus is also for forming a second component for a second hearing device, the apparatus comprising a second interior cavity and a second source of the second material for delivering the second material into the second interior cavity.

Optionally, the first source comprises a first syringe, and the second source comprises a second syringe.

Other and further aspects and features will be evident from reading the following detailed description.

BRIEF DESCRIPTION OF THE DRAWINGS

The drawings illustrate the design and utility of embodiments, in which similar elements are referred to by common reference numerals. In order to better appreciate how advantages and objects are obtained, a more particular description of the embodiments will be described with reference to the accompanying drawings. Understanding that these drawings depict only exemplary embodiments and are not therefore to be considered limiting in the scope of the claimed invention.

DESCRIPTION OF THE EMBODIMENTS

Figure 1:
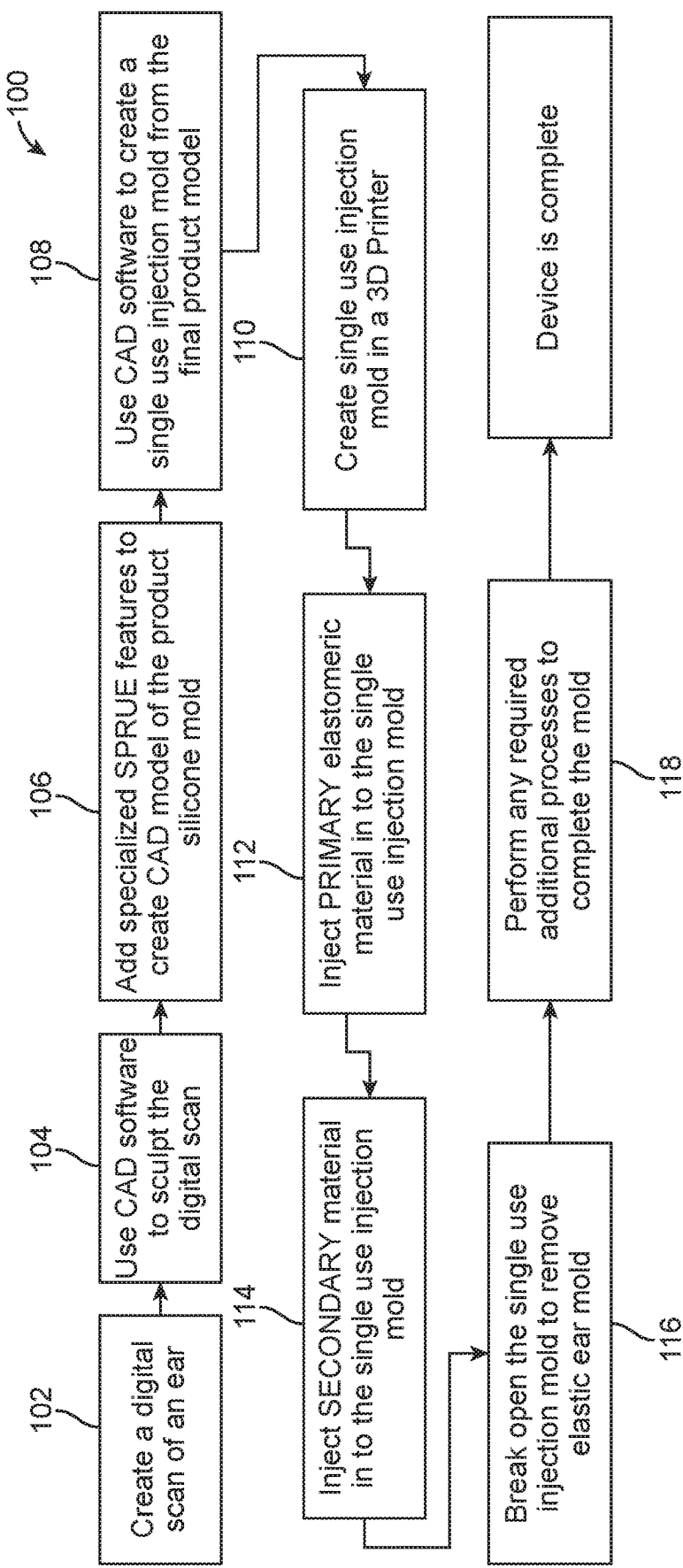
FIG. 1 illustrates a method of making a component of a hearing device.

Various embodiments are described hereinafter with reference to the figures. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages of the invention shown. An aspect or an advantage described in conjunction with a particular embodiment is not necessarily limited to that embodiment and can be practiced in any other embodiments even if not so illustrated or if not so explicitly described.

FIG. 1 illustrates a method 100 of creating a component of a hearing device. In the illustrated example, the component is a earpiece of the hearing device. However, in other embodiments, the component may be any other part of the hearing device. By means of non-limiting examples, the hearing device may be a hearing aid (such as in-the-ear hearing aid, completely-in-canal hearing aid, behind-the-ear hearing aid, etc.), an earphone, an earplug, an eardome, an earpiece for testing probe, an ear protection, etc.

As shown in the figure, first, a digital scan of an ear is created (item 102). Various techniques may be employed to obtain the digital scan. For example, a light-based scanning probe may be used to scan the ear. As another example, ultrasound-based scanning probe may be used to scan the ear. Handheld scanners known in the art may be employed in different embodiments. Also, an ear impression (e.g., a direct material cast of the ear cavity and shape) may be obtained, and the ear impression may then be scanned to create the digital scan for the ear. The digital scan may be embodied in a form of a digital file having data that represents features of the ear. The features of the ear may include interior cavity of the human ear canal and the outer ear areas. Also, in some embodiments, the data in the digital file may represent a shape of a concha, an outer ear canal, and an inner ear canal. In other embodiments, other techniques may be employed to create the digital file, which may or may not involve scanning of the ear.

Next, a computer-aid-design (CAD) software or tool is used to create a model of the ear based on the digital file (item 104). For example, the digital file may be converted into a CAD format to obtain a CAD model of the ear. The CAD tool may be used to modify the model of the ear. For example, certain undesirable features of the model may be deleted, certain parts of the model may be adjusted in shape and/or dimension, etc. The CAD software or tool may be any design tool that can be used in product design. For example, in some embodiments, the design tool may be eSculpting. In one implementation, the digital file representing features of the ear may be loaded into software (e.g., eSculpting) specifically configured for creating earmold products from digitally scanned images.

Next, sprue features are added to the CAD model of the ear to obtain a modified model of the ear (item 106). In some embodiments, the sprue features include a first sprue feature representing a first sprue for delivering a first material into the injection mold to be created, and a second sprue feature representing a second sprue for delivering a second material into the injection mold to be created. In other embodiments, the sprue features may include more than two sprue features. In some embodiments, the first sprue may include a cavity for containing the first material, and one or more channels or tubes for delivering the first material into the cavity of the injection mold to be created. Similarly, the second sprue may include a cavity for containing the second material, and one or more channels or tubes for delivering the second material into the cavity of the injection mold to be created. In some embodiments, item 106 is not required.

Next, the design tool may be used to obtain a model of the injection mold to be created (item 108). This injection mold model may be a digital representation of the injection mold. In some embodiments, the design tool may be configured to use the ear model or the modified ear model to create the injection mold model. Such may be accomplished by creating an offset from the ear model or the model of the device (i.e., the component of the hearing device) that is desired to be created. This results in a model of a hollow injection mold with the interior having the shape of the desired component to be created. In the illustrated embodiments, the created model of the injection mold also includes predesigned features of the sprues for both the first (primary) material and the second (secondary) material. In some embodiments, the sprues features are incorporated in item 106. In other embodiments, the features of the sprues may be inserted to the injection mold model in item 108 when the injection mold model is being created. In such cases, item 106 may not be required. In further embodiments, part(s) of the sprues features may be inserted in item 106, and other part(s) of the sprues features may be inserted in item 108.

In one implementation, eSculpting may be used to alter the shape of the ear model to create the shape of the injection mold model. The injection mold model includes objects for creating the sprues for the first material and the sprue for the second material.

Next, an injection mold is created based on the injection mold model (item 110). In the illustrated example, the injection mold is a single use injection mold. In such cases, after the component of the hearing device is created using the injection mold, the injection mold is destroyed in order to retrieve the created component. In other embodiments, the injection mold may not be a single use injection mold. For example, the injection mold may instead have multiple components that can be detachably coupled to each other. In such cases, after the component of the hearing device is made, the mold components may be detached from each other, and may then be reassembled to create the injection mold repeatedly. Also, in some embodiments, item 108 may be performed using a 3D printer, which receives the electronic file representing the injection mold, and creates the injection mold based on the received electronic file. The 3D printing process may be performed by any of a variety of 3D printers on the market today using a variety of materials. In some embodiments, the injection mold material may be chemically compatible with the material (e.g., first material) used to make the component of the hearing device.

After the injection mold is made, the injection mold may then be used to create the component of the hearing device. As shown in the figure, a first material (primary material) is first placed (e.g., injected) into the injection mold (item 112). The primary material may be an elastomer, or any of other types of materials that may be suitable for the component being created. By means of non-limiting examples, the first material may be silicone, urethane, etc. In the illustrated embodiments, because the injection mold has a first sprue configured to deliver the first material, the first sprue may be used to deliver the first material to an interior cavity of the injection mold. The first material may be injected into the injection mold until the entire interior surface, or substantially the entire interior surface, of the injection mold is covered by the first material.

Next, a second material (secondary material) is placed (e.g., injected) into the injection mold (item 114). The second material may be liquid, gel, foam, or any of other types of materials. By means of non-limiting examples, the second material may be silicone gel, silicone foam, urethane gel, urethane form, etc. In some embodiments, the second material has a characteristic (e.g., hardness, color, etc.) that is different from the characteristic of the first material. In the illustrated embodiments, because the injection mold has a second sprue configured to deliver the second material, the second sprue may be used to deliver the second material inside the injection mold.

In the illustrated embodiments, due to surface tension effect, the first material will adhere to the interior surface of the outer walls of the injection mold, while the second material is delivered into the injection mold. This allows the secondary material to occupy the interior of the injection mold without displacing the first material from the exterior or outer part of the injection mold cavity along the walls of the injection mold cavity. This allows the primary material to form the "outer" skin or layer of the component, while limiting the secondary material to the interior of the component. As a result, in the created component, the outer layer will have the advantages and features provided by the first material, while the interior part of the component will have the advantages and features provided by the second material.

In the illustrated embodiments, the second material is injected into the injection mold using the sprue(s) intended for the second material. This places the second material in specific locations chosen to optimize the performance of the injection mold and helps to balance the flow of the material into specific areas of the injection mold. In some cases, there may be multiple sprues located at different parts of the injection mold for delivering the second material into the injection mold. In some embodiments, the timing of injecting the second material via the one or more sprues, and/or injection pressure may be selected to affect the injection results. Also, in some embodiments, the amount of time allowed between the first and the second injections and/or a temperature of the process may affect the thickness of component part formed by the first material if the first material's curing reaction is time or temperature dependent.

The first and second materials are then cured to form the component. After the component of the hearing device is formed using the first and second materials, the component of the hearing device is then removed from the injection mold (item 116). In the illustrated example, the injection mold is a single use injection mold, and item 116 involves breaking the injection mold to remove the component of the hearing device from the injection mold. In other embodiments, the injection mold may include mold components that are detachably coupled to each other. In such cases, the mold components are separated from each other to remove the component of the hearing device.

Next, one or more additional processes may be performed on the component of the hearing device (item 118). For example, extra undesirable material attached to the component may be removed from the component by cutting, grinding, etc. Also, the surface of the component may be processed to create a desirable surface for the component. In other embodiments, item 118 is not required, and the component of the hearing device may be considered completed after item 116 is performed.

The component (e.g., the earmold in the example) of the hearing device made via the above technique has the first material located on the outer parts of the component, with the second material encased within the first material. In some embodiments, the first material may form a wall of an earmold, and the second material may be located in the wall and may be surrounded by the first material (e.g., the first material may form two opposite surfaces/layers of the wall, with the second material being sandwiched between the two layers of the first material). In some cases, the wall may surrounds a channel, wherein the channel is defined by the wall. In other embodiments, the first material may form the wall of the earmold, with the second material being located within a cavity of the earmold surrounded by the first material.

It should be noted that as used in this specification, the term "surrounded" or any of other similar terms refers to an item that is completely enclosed by another item, or that is substantially enclosed by another item. For example, when the second material is being described as "surrounded" by the first material, the second material may be completely enclosed by the first material, or may be substantially enclosed by the first material (e.g., at least 80%, 85%, 90%, 95%, or 99% of the surface area of the second material may be covered by the first material).

Figure 2:
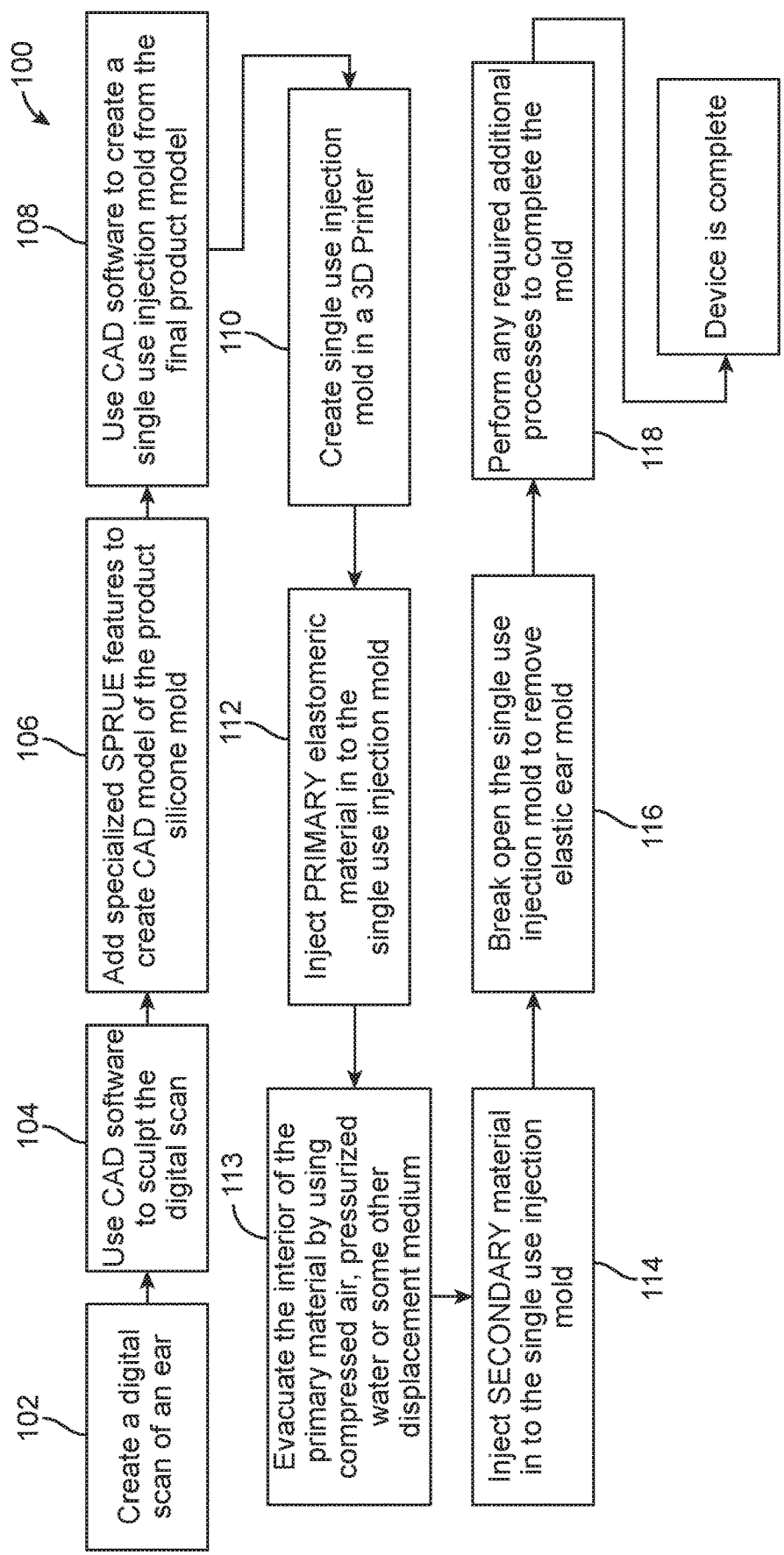
FIG. 2 illustrates another method of making a component of a hearing device, which includes using a medium for displacement of a primary material before adding a secondary material.

FIG. 2 illustrates another method 100 of creating a component of a hearing device. The method 100 of FIG. 2 is the same as that of FIG. 1, except that the method 100 of FIG. 2 further includes item 113 that is performed after item 112. In item 113, an interior of the first material is removed to create a cavity within the first material, wherein the second material can be later injected into the cavity within the first material (in item 114). In some embodiments, the act of removing the interior of the first material may comprise delivering liquid or air into the first material. In one implementation, the removal of the interior part of the first material may be accomplished by using a medium that displaces the interior portion of the first material. The medium may be compressed air or pressurized liquid to evacuate the interior of the first material. The second material is then injected into the injection mold through the sprue(s) and fills the evacuated interior. The method 100 of FIG. 2 achieves more displacement of the first material, allowing for more of the second material to be placed in the final device interior. Time and/or injection pressure may also be used to affect the injection results.

In the above embodiments, the sprues are described as being attached to the mold that are formed together with the mold. In other embodiments, the sprues may be separately formed from the mold, and may not be integrally formed with the mold.

Figure 3:
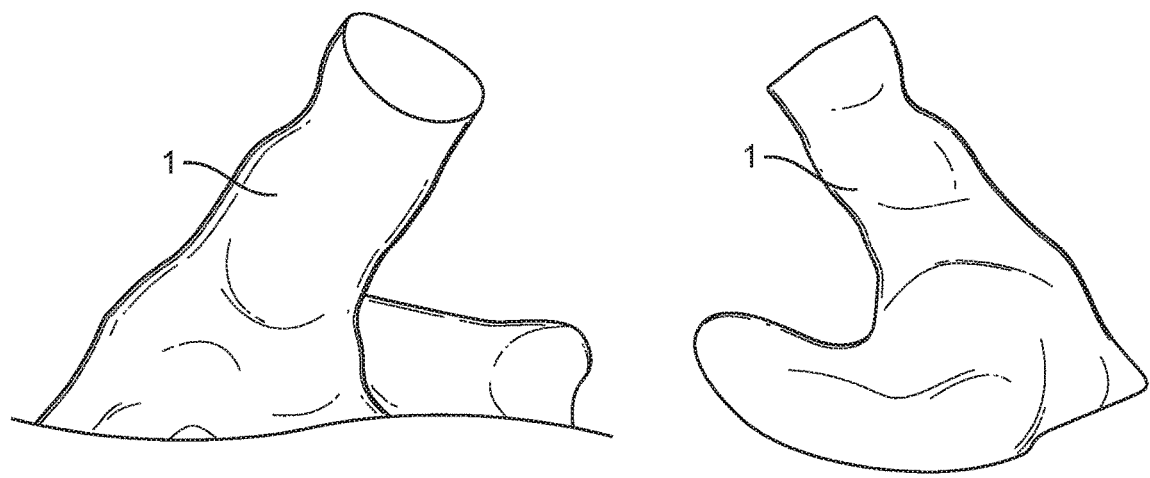
FIG. 3 illustrates an ear impression captured with digital 3D scanning. This is the starting point image for creating the component of the hearing device. This figure shows an anterior view (right) and a posterior view (left) of the canal/inner ear.

FIG. 3 illustrates an ear impression (1) captured with digital 3D scanning. This is the starting point image for creating the component of the hearing device (e.g., earphone device). This figure shows an anterior view (right) and a posterior view (left) of the canal/inner ear.

Figure 4:
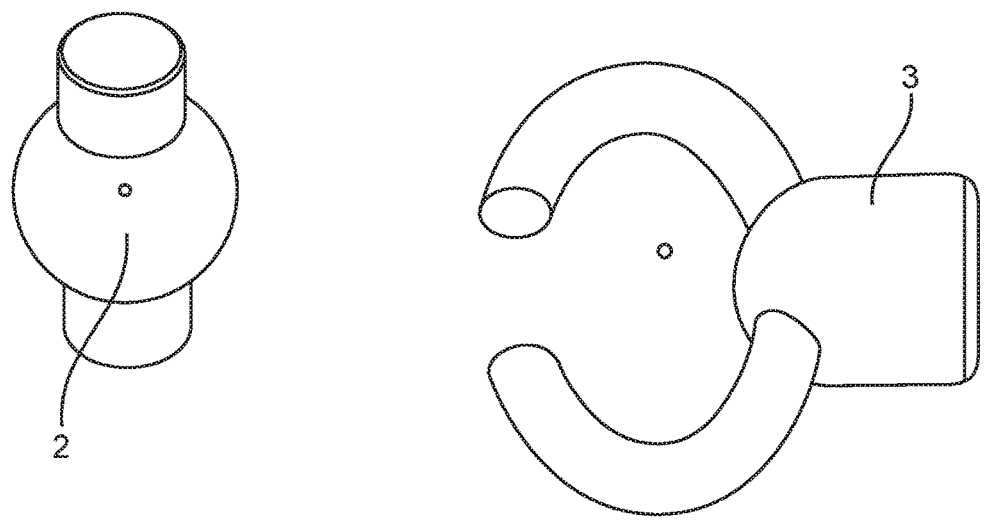
FIG. 4 illustrates sprues for injecting primary material and secondary material into a mold.

FIG. 4 illustrates sprues (2 & 3) for injecting primary material and secondary material into the injection mold (4).

Figure 5:
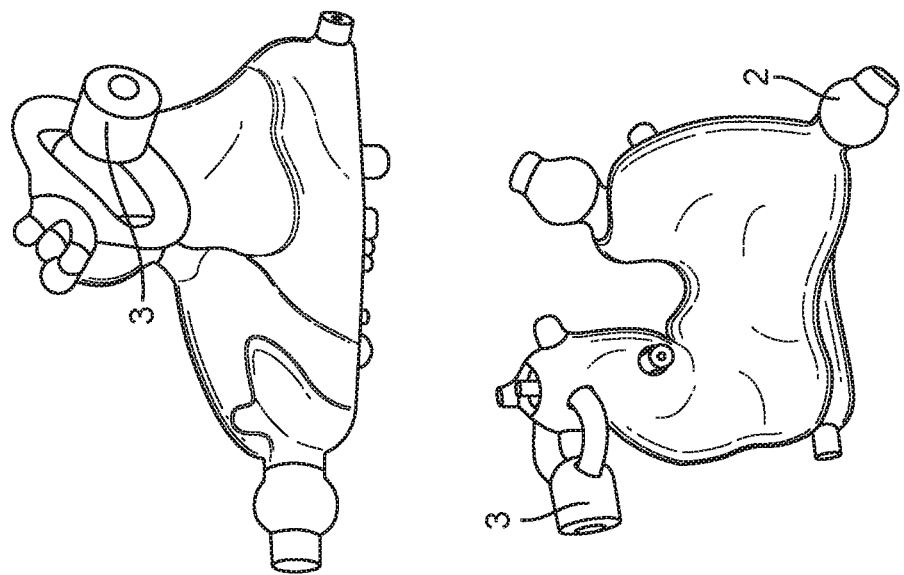
FIG. 5 illustrates a single use injection mold, having two injection ports to allow the creation of a composite mold from two different materials such as soft and hard, or different colors.
Figure 5:
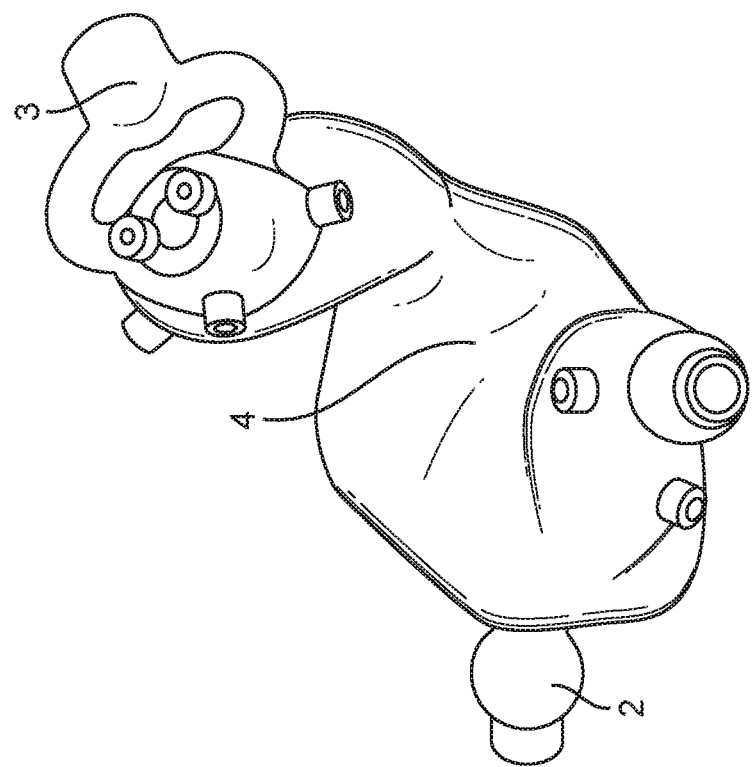

FIG. 5 illustrates different views of an injection mold (4) showing the two injection ports (2,3) to allow the creation of a composite earmold from two different materials such as soft and hard, or different colors.

Figure 6:
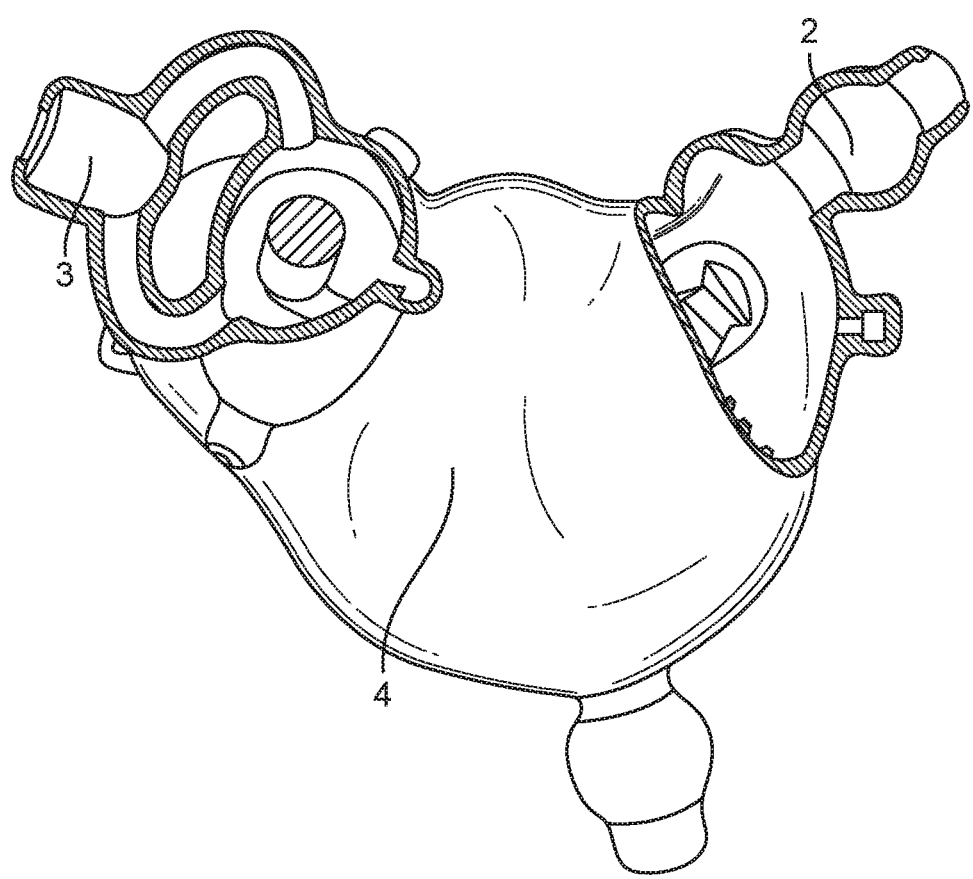
FIG. 6 illustrates a cross sectional view of the injection mold of FIG. 5, configured to create an earmold, particularly showing how the sprues are configured to introduce material into the single use injection mold.

FIG. 6 illustrates a cross section view of the injection mold (4) of FIG. 5 used to create the earmold (5), particularly showing how the sprues (2, 3) are used to introduce material into the injection mold (4).

Figure 7:
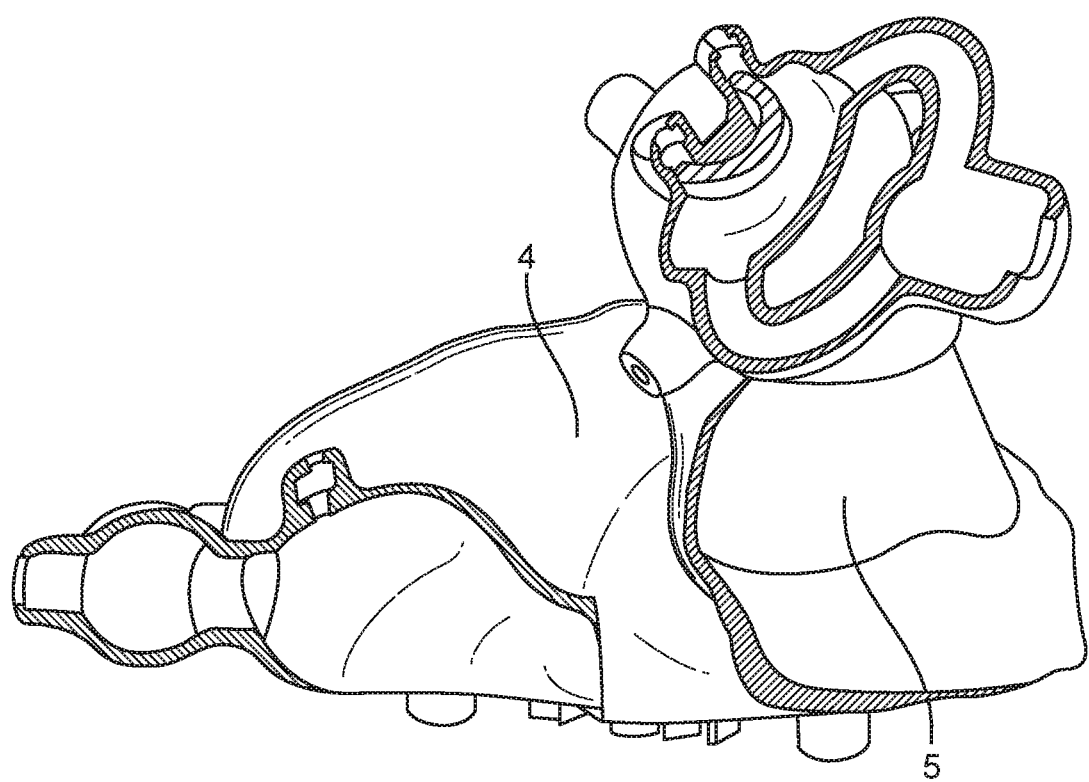
FIG. 7 illustrates an earmold inside of the single use injection mold during a "demolding" step of removing the earmold from the single use injection mold.

FIG. 7 illustrates the earmold (5) shown inside of the injection mold (4) during the "demolding" step of removing the earmold from the injection mold (4).

Figure 8:
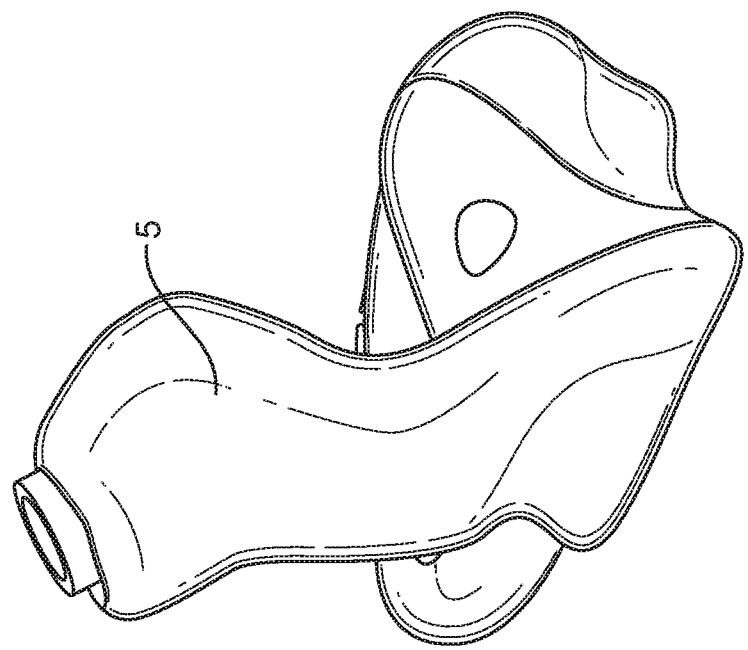
FIG. 8 illustrates an example of a device (e.g., a component of a hearing device) made from a primary material of either silicone or silicone elastomer that is infused with an interior of a secondary material such as foam, gel, or a elastomer of a different hardness or characteristic from the primary material.
Figure 8:
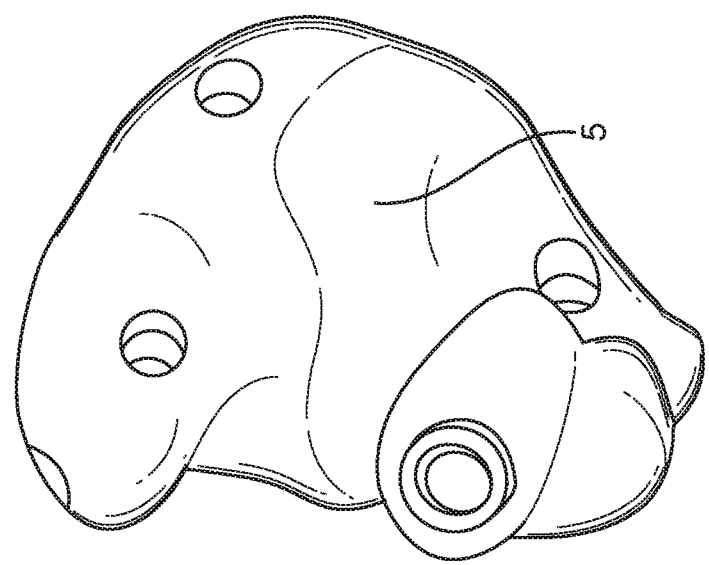

FIG. 8 illustrates the earmold (5) made from a primary material of either silicone or silicone elastomer that is infused with an interior of a secondary material such as foam (6), gel, or a elastomer of a different hardness or characteristic from the primary.

Figure 9:
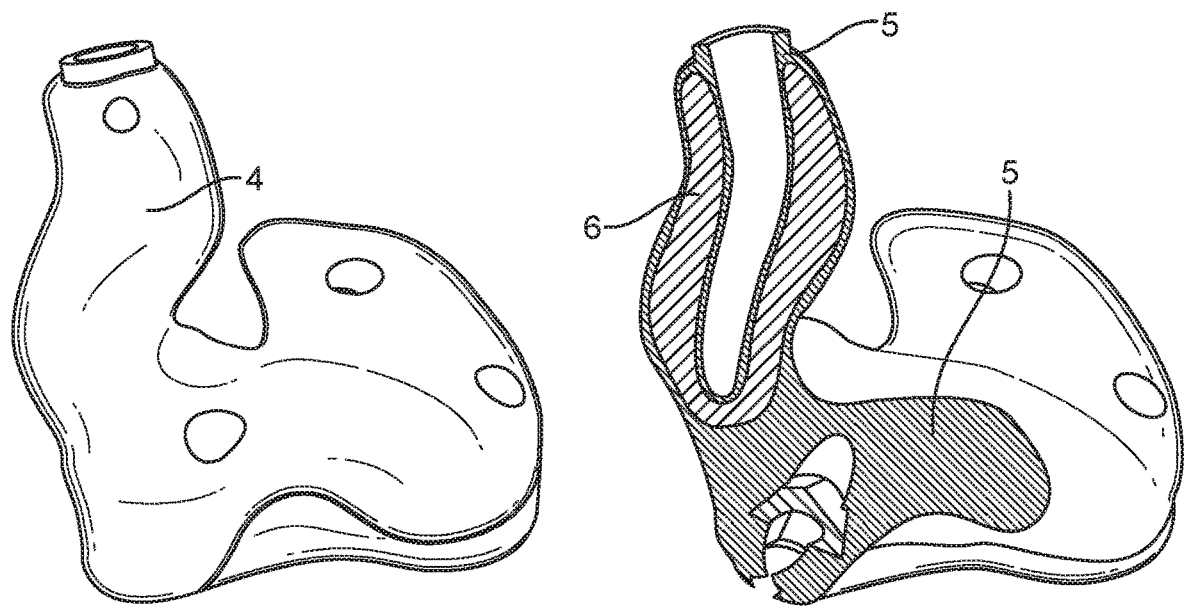
FIG. 9 illustrates the device of FIG. 8 as shown from the inferior view (left) and with a cross section through the anterior view to show the location of the primary and secondary materials. The primary material remains in areas where it was in contact with the injection mold wall, but is displaced in specific areas by the secondary material.

FIG. 9 illustrates the earmold (5) as shown from the inferior view (left) and with a cross section through the anterior view to show the location of the primary and secondary materials (7). The primary material (6) remains in areas where it was in contact with the injection mold interior wall, but is displaced in specific areas by the secondary material (7).

Figure 10:
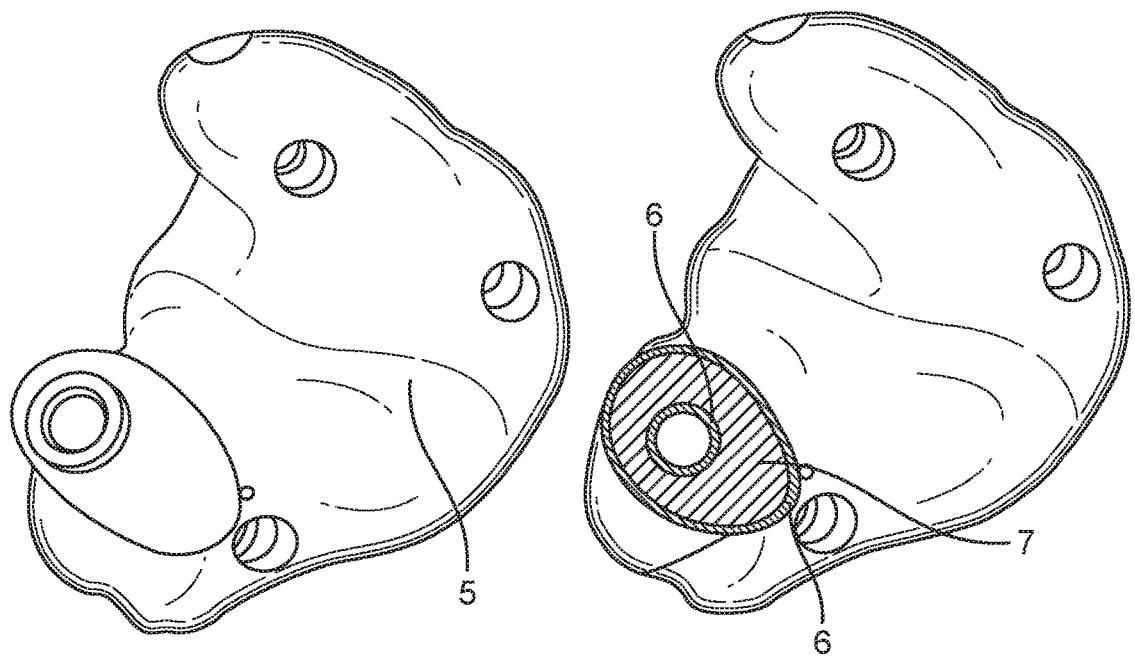
FIG. 10 illustrates the device of FIG. 8 as shown from the end of the ear canal (left) with a cross section through the canal view to show the location of the primary and secondary materials. The primary material remains in areas where it was in contact with the injection mold wall, but is displaced in specific areas by the secondary material.

FIG. 10 illustrates the earmold (5) as shown from the end of the ear canal (left) with a cross section through the canal view to show the location of the primary (6) and secondary materials (7). The primary material (6) remains in areas where it was in contact with the injection mold interior wall, but is displaced in specific areas by the secondary material (7).

Figure 11:
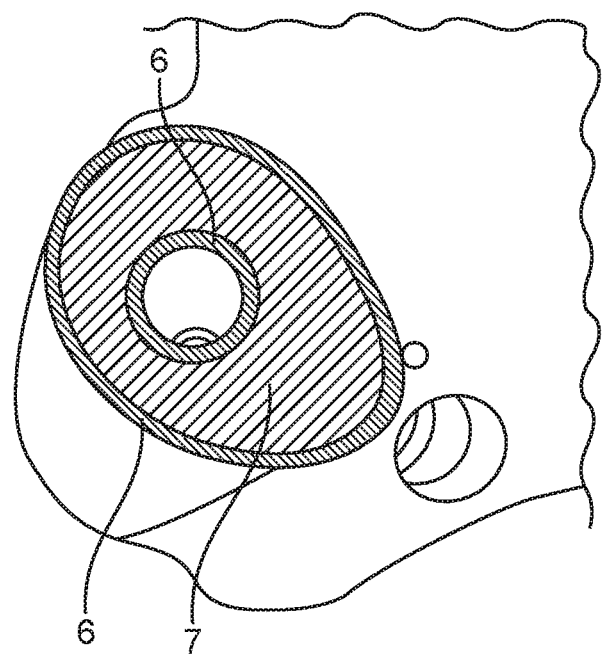
FIG. 11 illustrates the device of FIG. 8 as shown from the end of the ear canal (left) with a cross section through the canal view to show the location of the primary and secondary materials.

FIG. 11 illustrates the earmold (5) as shown from the end of the ear canal (left) with a cross section through the canal view to show the location of the primary (6) and secondary (7) materials.

Figure 12:
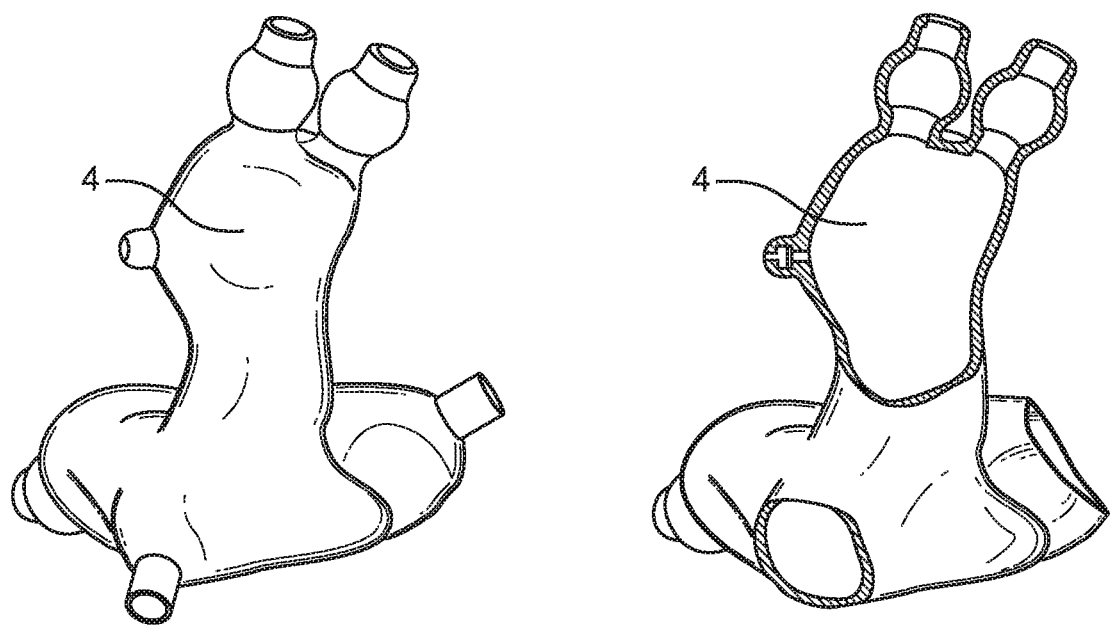
FIG. 12 illustrates another example of a single use injection mold and a cutaway section of the single use injection mold.

FIG. 12 illustrates another injection mold (4) and a cutaway section of the injection mold (4).

Figure 13:
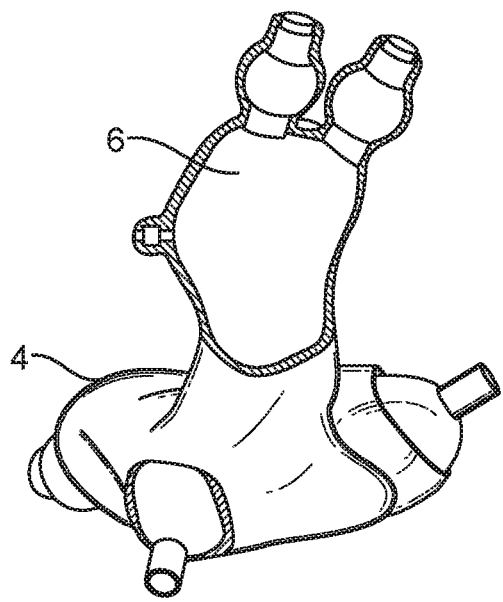
FIG. 13 illustrates the injection mold of FIG. 12 filled with a primary material.

FIG. 13 illustrates the injection mold (4) of FIG. 12, filled with the primary material (6).

Figure 14:
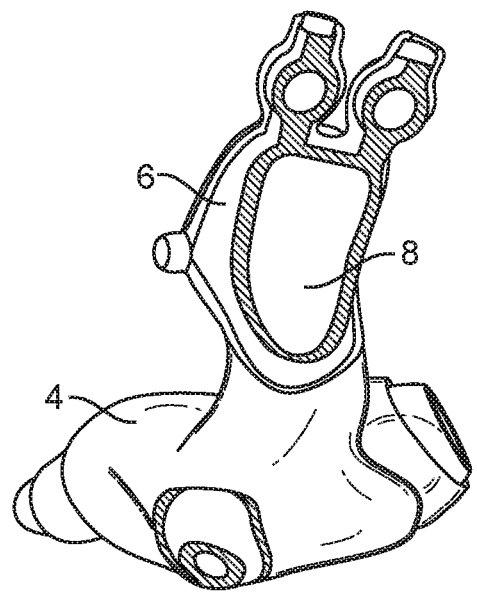
FIG. 14 illustrates the injection mold of FIG. 12 filled with the primary material, and the interior area of the primary material has been displaced with air or water to create a hollow area in the primary material.

FIG. 14 illustrates the injection mold (4) of FIG. 12, filled with the primary material (6), and the interior area of the primary material (5) has been displaced with air or water to create a hollow area (8) in the primary material (6).

Figure 15:
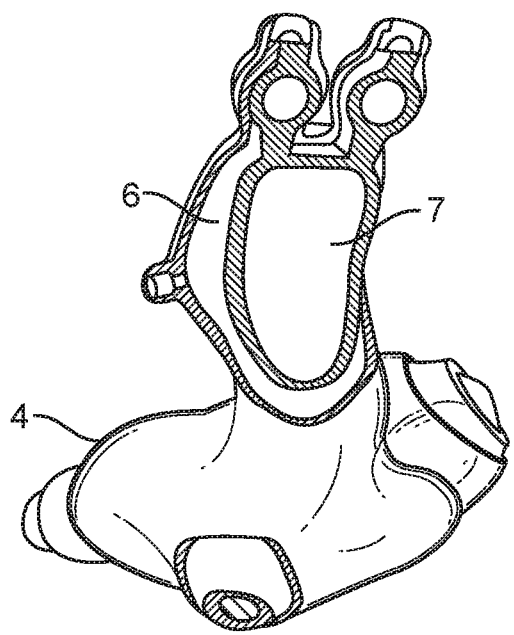
FIG. 15 illustrates the injection mold of FIG. 12 filled with the evacuated primary material forming a thin wall against the interior surface of the injection mold. The evacuated interior is filled with a secondary material to form a compliant interior.

FIG. 15 illustrates the injection mold (4) filled with the evacuated primary material (6) forming a thin wall against the side of the injection mold (4). The evacuated interior is filled with the secondary material (7) to form a compliant interior.

In some embodiments, the second material may be configured (e.g., selected and/or positionally designed) to improve a bass effect associated with the hearing device. Also, in some embodiments, the second material may be configured to provide an acoustic seal by attenuating external sounds. Furthermore, in some embodiments, the second material may be configured to reduce an occlusion effect associated with the hearing device.

The above techniques for creating the earmold (5) are advantageous. By utilizing the abilities of application specific software and 3D printing, the earmold (5) achieved is a sophisticated composite structure combining a variety of materials to enhance the properties, performance and appearance of the resulting earmold (5). Also, interior features of the earmold (5) are no longer limited to a set arrangement of interior spaces. Rather, the earmold (5) has customized outer shape, and also customized arrangement of the inner characteristics.

Figure 16:
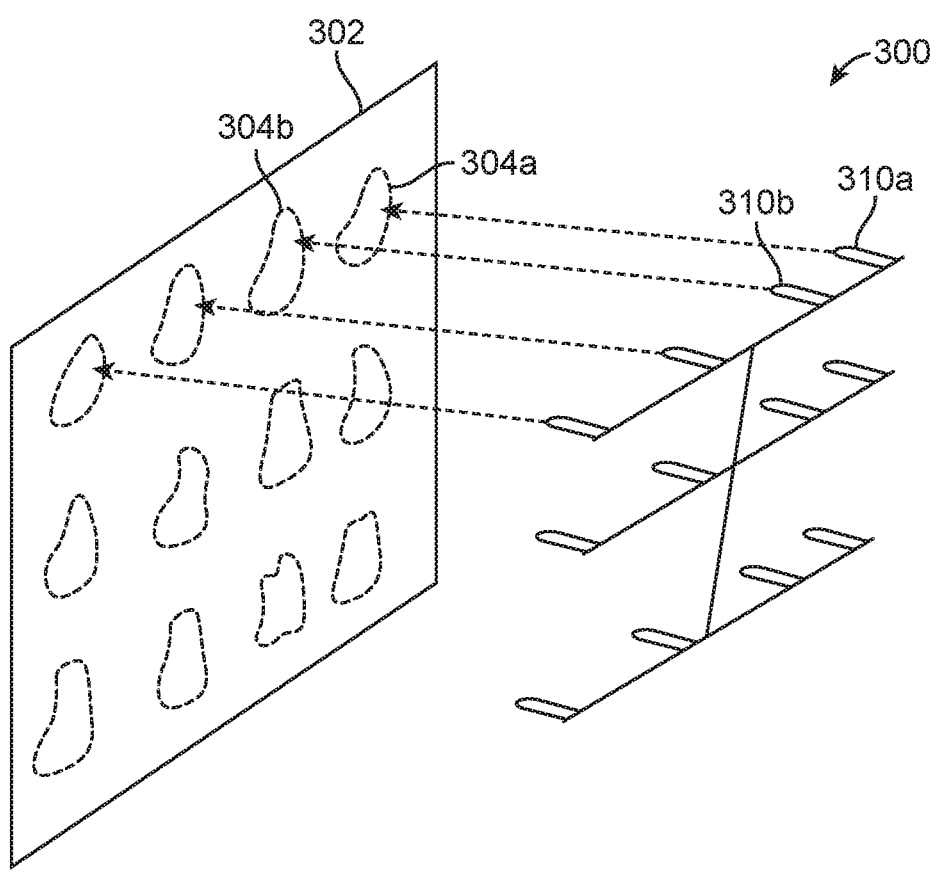
FIG. 16 illustrates another apparatus for forming one or more components of one or more hearing devices.

FIG. 16 illustrates another apparatus 300 for forming one or more components of one or more hearing devices.

In some embodiments, the one or more hearing devices include a first hearing device. The one or more components include a first component comprising an earpiece having a housing, the housing comprising a wall made from a first material, wherein the wall of the housing comprises a second material surrounded by the first material. In the illustrated embodiments, the apparatus 300 includes a mold 302 having a first interior cavity 304a for containing the first material and the second material, wherein the mold 302 comprises a first port configured to receive the first material. The apparatus 300 also includes a first source 310a of the second material for delivering the second material into the first interior cavity 304a so that the second material is within the first material.

In the illustrated embodiments, the apparatus 300 is also for forming a second component for a second hearing device. The apparatus 300 includes a second interior cavity 304b and a second source 310b of the second material for delivering the second material into the second interior cavity.

In some embodiments, the first source 310a of the second material comprises a first syringe. As used in this specification, the term "syringe" may refer to any fluid delivery device that includes a container for housing fluid.

Also, in some embodiments, the first source 310a comprises a first syringe, and the second source 310b comprises a second syringe.

In some embodiments, the cavities 304 are for forming respective components for respective hearing devices. Each cavity 304 is configured to receive a first material, and a second material so that the second material is surrounded by the first material. In some cases, the mold 302 includes multiple first ports for allowing the first material to be delivered into the respective cavities 304. The first ports may also allow the second material to be delivered into the respective cavities 304. Alternatively, the mold 302 may include multiple second ports for allowing the second material to be delivered into the respective cavities. In addition, in some embodiments, the apparatus 300 may include multiple syringes for simultaneously injecting the second material into the respective cavities 304. In such cases, the syringes are arranged in relative positions that correspond with the positions of the respective cavities 304. The syringes may be mounted to a common positioner, which is configured to move all of the syringes simultaneously so that the injection ends of the syringes are moved into respective ports of the mold 302 that are in fluid communication with the respective interior cavities 304.

It should be noted that the above techniques are not limited to creating customized components for hearing devices. In other embodiments, the above techniques may be employed to create standard components for hearing devices, or components that have both customized and non-customized features. For example, in other embodiments, the exterior shape of the earmold (5) may be standard, while the interior characteristics are customized.

Also, the above techniques may be employed to create components for a variety of hearing devices, and not just the examples illustrated in the figures. By means of non-limiting examples, the techniques described herein may be employed to create components for hearing aids (such as in-the-ear hearing aids, completely-in-canal hearing aids, behind-the-ear hearing aids, etc.), earphones, earplugs, eardomes, earpieces for testing probes, ear protection, etc.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

What is claimed:

1. An apparatus for forming a component for a hearing device, the component comprising an earpiece having a wall made from a first material and a second material, the apparatus comprising:

a mold having an interior cavity for containing the first material and the second material;

wherein the mold comprises a first port configured to receive the first material;

wherein the mold comprises a second port configured to receive the second material, and a first channel for directing the second material to displace some of the first material while the first material is in uncured form;

wherein the mold is configured to form the wall that surrounds and defines an earpiece channel, the wall having a first layer and a second layer opposite from the first layer, wherein the mold is configured to form the first and second layers using at least some of the first material, wherein the wall further has a core layer disposed between the first layer and the second layer, the core layer formed by at least some of the second material, and wherein the wall that has the first layer, the core layer, and the second layer surrounds and defines the earpiece channel.

2. The apparatus of claim 1, wherein the mold comprises a single-use mold.

3. The apparatus of claim 1, further comprising a first source of the first material.

4. The apparatus of claim 3, wherein the first material comprises silicone or urethane.

5. The apparatus of claim 3, further comprising a second source of the second material.

6. The apparatus of claim 5, wherein the mold also comprises a second channel for directing the second material to within the first material to form the core layer between the first layer and the second layer of the wall that defines the earpiece channel.

7. The apparatus of claim 5, wherein the second material comprises silicone gel, silicone foam, urethane gel, or urethane foam.

8. The apparatus of claim 5, wherein the second material comprises liquid.

9. The apparatus of claim 5, wherein the second material comprises foam.

10. The apparatus of claim 5, wherein the second material comprises air.

11. The apparatus of claim 5, wherein the second material comprises gel.

12. The apparatus of claim 5, wherein the second material comprises silicone or urethane.

13. The apparatus of claim 1, further comprising a source of liquid or air for displacing some of the first material after the first material is delivered inside the mold.

14. The apparatus of claim 1, wherein the mold comprises a custom mold.

15. The apparatus of claim 1, wherein the first channel is configured to direct the second material to within the first material while the first material is in uncured form.

16. An earpiece made from a process that involves the apparatus of claim 1, the process comprising:
- placing the first material in the interior cavity of the mold through the first port; and
- placing the second material in the interior cavity of the mold through the second port so that the second material is within the first material;
- wherein at least some of the first material forms the first layer and the second layer of the wall that defines the earpiece channel, and wherein at least some of the second material forms the core layer of the wall of the earpiece.

17. The apparatus of claim 1, wherein the mold comprises a first mold part configured to define a surface of the first layer of the wall, and wherein the mold also comprises a second mold part configured to define a surface of the second layer of the wall.

18. The apparatus of claim 17, wherein the first mold part comprises a mold housing.

19. The apparatus of claim 18, wherein the second mold part comprises a block, and wherein at least a part of the block is located inside the mold housing and is spaced away from an inner surface of the mold housing.

20. The apparatus of claim 19, wherein a spacing between the mold housing and the block is configured to accommodate the at least some of the first material for forming the first and second layers of the wall, and the at least some of the second material for forming the core layer of the wall.

21. An apparatus for forming a first component for a first hearing device, the first component comprising an earpiece having a wall made from a first material and a second material, the apparatus comprising:
- a mold having a first interior cavity for containing the first material and the second material, wherein the mold comprises a first port configured to receive the first material;
- wherein the mold is configured to couple to a first source of the first material;
- wherein the mold is configured to couple to a second source of the second material, wherein the mold is configured to receive the second material to displace some of the first material while the first material is in uncured form; and
- wherein the mold is configured to form the wall that surrounds and defines an earpiece channel, the wall having a first layer and a second layer opposite from the first layer, wherein the mold is configured to form the first and second layers using at least some of the first material, wherein the wall further has a core layer disposed between the first layer and the second layer, the core layer formed by at least some of the second material, and wherein the wall that has the first layer, the core layer, and the second layer surrounds and defines the earpiece channel.

22. The apparatus of claim 21, wherein the first source of the first material comprises a first syringe.

23. The apparatus of claim 22, wherein the second source of the second material comprises a second syringe.

24. The apparatus of claim 21, wherein the apparatus is also for forming a second component for a second hearing device.

25. The apparatus of claim 21, wherein the second material is different from the first material, the apparatus further comprising a channel configured to direct the second material to within the first material of the wall that defines the earpiece channel.

26. The apparatus of claim 21, wherein the mold comprises a channel configured to direct the second material into the first material while the first material is in uncured form.

27. The apparatus of claim 21, wherein the mold comprises a custom mold.

28. The apparatus of claim 21, wherein the mold comprises a first mold part configured to define a surface of the first layer of the wall, and wherein the mold also comprises a second mold part configured to define a surface of the second layer of the wall.

29. The apparatus of claim 28, wherein the first mold part comprises a mold housing.

30. The apparatus of claim 29, wherein the second mold part comprises a block, and wherein at least a part of the block is located inside the mold housing and is spaced away from an inner surface of the mold housing.

31. The apparatus of claim 30, wherein a spacing between the mold housing and the block is configured to accommodate the at least some of the first material for forming the first and second layers of the wall, and the at least some of the second material for forming the core layer of the wall.

32. The apparatus of claim 21, wherein the second material comprises liquid, foam, air, or gel.

33. The apparatus of claim 21, wherein the second material comprises silicone.

34. The apparatus of claim 21, wherein the second material comprises urethane.

\* \* \* \* \*